(12) United States Patent
Bogoni et al.

(10) Patent No.: US 9,401,047 B2
(45) Date of Patent: Jul. 26, 2016

(54) ENHANCED VISUALIZATION OF MEDICAL IMAGE DATA

(75) Inventors: Luca Bogoni, Philadelphia, PA (US); Gerardo Hermosillo Valadez, West Chester, PA (US); Matthias Wolf, Coatesville, PA (US)

(73) Assignee: Siemens Medical Solutions, USA, Inc., Malvern, PA (US)

(*) Notice: Subject to any disclaimer, the term of this patent is extended or adjusted under 35 U.S.C. 154(b) by 114 days.

(21) Appl. No.: 13/086,448

(22) Filed: Apr. 14, 2011

(65) Prior Publication Data

US 2011/0255763 A1    Oct. 20, 2011

Related U.S. Application Data

(60) Provisional application No. 61/324,361, filed on Apr. 15, 2010.

(51) Int. Cl.
```
G06K 9/00      (2006.01)
G06T 19/00     (2011.01)
A61B 6/02      (2006.01)
```
(52) U.S. Cl.
CPC ............... *G06T 19/00* (2013.01); *A61B 6/027* (2013.01); *G06T 2210/41* (2013.01); *G06T 2219/2012* (2013.01)

(58) Field of Classification Search
CPC .... A61B 6/027; G06T 19/00; G06T 2210/41; G06T 2219/2012
See application file for complete search history.

(56) References Cited

U.S. PATENT DOCUMENTS

| | | | | |
|---|---|---|---|---|
| 5,335,298 | A * | 8/1994 | Hevenor et al. | 382/199 |
| 5,782,762 | A * | 7/1998 | Vining | 600/407 |
| 6,346,940 | B1 * | 2/2002 | Fukunaga | G06T 15/20 345/420 |
| 6,608,916 | B1 * | 8/2003 | Wei et al. | 382/132 |
| 6,621,918 | B1 * | 9/2003 | Hu | G06F 19/321 382/128 |
| 6,625,303 | B1 * | 9/2003 | Young et al. | 382/132 |
| 6,707,878 | B2 * | 3/2004 | Claus et al. | 378/22 |
| 6,819,785 | B1 * | 11/2004 | Vining | G06F 17/30056 128/922 |
| 6,928,314 | B1 * | 8/2005 | Johnson | G06T 7/606 128/920 |
| 6,985,612 | B2 * | 1/2006 | Hahn | 382/128 |
| 7,640,050 | B2 * | 12/2009 | Glenn et al. | 600/407 |
| 7,706,600 | B2 * | 4/2010 | Kreeger | G06T 7/0083 345/419 |
| 7,734,119 | B2 * | 6/2010 | Cheryauka et al. | 382/302 |
| 8,005,283 | B2 * | 8/2011 | John et al. | 382/130 |
| 8,009,883 | B2 * | 8/2011 | Ying et al. | 382/128 |
| 8,144,956 | B2 * | 3/2012 | Salgo et al. | 382/128 |
| 8,150,111 | B2 * | 4/2012 | Borland et al. | 382/128 |
| 8,155,416 | B2 * | 4/2012 | Nields et al. | 382/131 |

(Continued)

OTHER PUBLICATIONS

Williams ("Volumetric Curved Planar Reformation for Virtual Endoscopy", Jan. 2008 IEEE Transactions on Visualization and Computer Graphics.*

(Continued)

*Primary Examiner* — Avinash Yentrapati
(74) *Attorney, Agent, or Firm* — Peter R. Withstandley (57) ABSTRACT

Described herein is a technology for enhanced visualization of medical image data. In one implementation, a region of interest is identified in a first set of images along at least one viewing direction. Based on the first set of images, a second set of images is reconstructed to include at least one selectively enhanced rendering of the region of interest. The selectively enhanced rendering may include a three-dimensional rendering or any other type of enhanced rendering to facilitate detection of abnormalities.

24 Claims, 5 Drawing Sheets

(56) References Cited

U.S. PATENT DOCUMENTS

| | | | | |
|---|---|---|---|---|
| 8,184,890 | B2* | 5/2012 | Zhang | A61B 6/463 128/922 |
| 2003/0053673 | A1* | 3/2003 | Dewaele | 382/132 |
| 2005/0024724 | A1* | 2/2005 | Kim | G06T 15/08 359/462 |
| 2005/0119550 | A1* | 6/2005 | Serra | G06T 19/00 600/407 |
| 2007/0047794 | A1* | 3/2007 | Lang et al. | 382/132 |
| 2007/0172104 | A1* | 7/2007 | Nishide et al. | 382/131 |
| 2007/0271122 | A1* | 11/2007 | Zaleski | A61B 5/1113 705/3 |
| 2007/0276214 | A1* | 11/2007 | Dachille | G06T 7/0012 600/407 |
| 2008/0049991 | A1* | 2/2008 | Gering | 382/128 |
| 2008/0193002 | A1* | 8/2008 | Ying et al. | 382/131 |
| 2009/0128553 | A1* | 5/2009 | Perry et al. | 345/419 |
| 2009/0136109 | A1* | 5/2009 | Salgo et al. | 382/131 |
| 2009/0169087 | A1* | 7/2009 | Doi | G06T 7/0012 382/132 |
| 2009/0196480 | A1* | 8/2009 | Nields et al. | 382/132 |
| 2010/0040200 | A1* | 2/2010 | Ema et al. | 378/98.12 |
| 2011/0063288 | A1* | 3/2011 | Valadez | G06T 15/08 345/419 |
| 2011/0069063 | A1* | 3/2011 | Liao et al. | 345/419 |
| 2011/0125016 | A1* | 5/2011 | Lazebnik et al. | 600/443 |
| 2011/0222750 | A1* | 9/2011 | Liao | A61B 6/4441 382/131 |
| 2011/0228997 | A1* | 9/2011 | Sharp et al. | 382/131 |
| 2011/0286630 | A1* | 11/2011 | Harder et al. | 382/103 |
| 2012/0089015 | A1* | 4/2012 | Gagnon | A61B 6/037 600/425 |
| 2015/0036908 | A1* | 2/2015 | Wiemker | G06T 7/0012 382/131 |

OTHER PUBLICATIONS

Straka et al ("The VesselGlyph: Focus and Context Visualization in CT angiography", IEEE 2004).*

Ganser et al ("A deformable digital brain atlas system according to Talairach and Tournoux", Medical Image Analysis 8 (2004) 3-22).*

Seemann et al ("Evaluation of the middle and inner ear structures: comparison of hybrid rendering, virtual endoscopy and axial 2D source images", Eur. Radiol. 9, 1851±1858 (1999).*

Scott R. Paulsen, et al., "CT Enterography as a Diagnostic Tool in Evaluating Small Bowel Disorders: Review of Clinical Experience with over 700 Cases", Radiographics. May-Jun. 2006; 26(3):641-57; discussion 657-62.

M. Sabry Hassouna, et al., "Virtual Fly-Over: A New Visualization Technique for Virtual Colonoscopy", Med Image Comput Comput Assist Interv. 2006; 9(Pt 1):381-8.

Stuart A Taylor, et al., "Polyp Detection with CT Colonography: Primary 3D Endoluminal Analysis versus Primary 2D Transverse Analysis with Computer-assisted Reader Software", Radiology. Jun. 2006; 239(3):759-67. Epub Mar. 16, 2006.

Davide Ippolito, et al., "MR enterography with polyethylene glycol as oral contrast medium in the follow-up of patients with Crohn disease: comparison with CT enterography", Abdom Imaging. Jul. 7, 2009.

James E. East, et al., "Uni- and bidirectional wide angle CT colonography: effect on missed areas, surface visualization, viewing time and polyp conspicuity", Eur Radiol. Sep. 2008; 18(9): 1910-7. Epub 208 Apr. 15.

James E East, et al., "Surface Visualization at CT Colonography Simulated Colonoscopy: Effect of Varying Field of View and Retrograde View", Am J Gastroenterol. Nov. 2007; 102(11):2529-35. Epub Jul. 19, 2007.

Emanuele Neri et al., "Time efficiency of CT colonogrpahy: 2D vs 3D visualization", Comput Med Imaging Graph. Apr. 2006;30(3): 175-80. Epub May 26, 2006.

J Wessling, et al., "CT Kolonographie: Techniken der Visualisierung und Befundung", Radiologe. Feb. 2008; 48(2): 135-4.

Thoams Mang, et al., "Comparison of axial, coronal, and primary 3D review in MDCT colonography for the detection of small polyps: A phantom study", Eur J Radiol. Apr. 2009; 70(1): 86-93. Epub Jan. 24, 2008.

Patricia Carrascosa, et al., "Multidetector CT colonoscopy: evaluation of the perspective-filet view virtual colon dissection technique for the detection of elevated lesions", Abdom Imaging. Sep.-Oct. 2007; 32(5):582-8.

Hetal Dave-Verma, et al., "Computed Tomographic Enterography and Enteroclysis: Pearls and Pitfalls", Curr Probl Diagn Radiol. Nov.-Dec. 2008; 37(6): 279-87.

V.A. Fisichella, et al., "Primary Three-Dimensional Analysis with Perspective-Filet View Versus Primary Two-Dimensional Analysis: Evaluation of Lesion Detection by Inexperienced Readers at Computed Tomographic Colonography in Symptomatic Patients", Acta Radiol. Apr. 2009; 50(3): 244-55.

David Williams, et al., "Volumetric Curved Planar Reformation of Virtual Endoscopy", IEEE Trans Vis Comput Graph. Jan.-Feb. 2008;14(1):109-19.

Abraham H. Dachman, et al., "CT Colonography: Visualization Methods, Interpretation, and Pitfalls", Radiol Clin North Am. Mar. 2007;45(2):347-59.

Bernhard Geiger, et al., "Panoramic Views for Virtual Endoscopy", Med Image Comput Comput Assist Interv. 2005;8(Pt 1):662-9.

* cited by examiner

ENHANCED VISUALIZATION OF MEDICAL IMAGE DATA

CROSS-REFERENCE TO RELATED APPLICATION

The present application claims the benefit of U.S. provisional application No. 61/324,361 filed Apr. 15, 2010, the entire contents of which are herein incorporated by reference.

TECHNICAL FIELD

The present disclosure relates generally to systems and methods for enhanced visualization of medical image data, and more specifically, to visualization of medical images in which one or more regions of interest have been enhanced by rendering.

BACKGROUND

In the field of medical imaging, various systems have been developed for generating medical images of various anatomical structures of individuals for the purpose of screening and evaluating medical conditions. These imaging systems include, for example, computed tomography (CT) imaging systems, magnetic resonance imaging (MRI) systems, X-ray systems, ultrasound systems, positron emission tomography (PET) systems, and single photon emission computed tomography (SPECT) systems, etc. For example, computed tomography (CT) imaging systems can be used to acquire a volumetric dataset of cross-sectional images or two-dimensional (2D) "slices" that cover an anatomical part. Each imaging modality may provide unique advantages over other modalities for screening and evaluating certain types of diseases, medical conditions or anatomical abnormalities.

The acquired images are reviewed to identify any lesions, medical conditions or abnormal anatomical structures, such as cancer, polyps, etc. One conventional method of review is by manually looking at hard copies (e.g., X-ray films, prints, photographs, etc.) of the acquired images to discern characteristic features of interest. For example, a trained radiologist may view a film image attached to a light board to identify potential abnormal anatomical structures or lesions. However, such manual review process is very time consuming and prone to human error.

To assist interpretation of medical images, various visualization systems and tools have been developed. The acquired images are typically digitized for viewing directly on viewing stations, either as part of an electronic picture archiving and communication (PAC) system, standalone workstations or even communication devices (e.g., phones, personal digital assistants, etc.). Commonly used methods to view these datasets include two-dimensional (2D) or slice-by-slice viewing, and three-dimensional (3D) viewing. For cases involving hollow or tubular structures (e.g., airways, colon, blood vessels, etc.), such visualization typically tries to simulate the real inspection of the desired structure and is commonly referred to as a virtual flythrough.

In the 2D or slice-by-slice viewing mode, the 2D images are rendered by projecting volumetric data along principal orthogonal directions onto an axial, coronal or sagittal viewing plane. The user typically browses through numerous 2D images in search of abnormal structures or medical conditions by manually scrolling up and down a stack of axial images following a mental image of the anatomical structure. Although the 2D reading mode is most commonly used in clinical radiological review, inherent limitations do exist. For example, abnormal structures are often easily missed because they are usually not visible in most of the 2D images and appear only very subtly. In the context of virtual colonoscopy (e.g., CT colonography) for colon cancer screening, for instance, polyps are often missed since they appear or disappear very quickly in the scrolling process. In addition, 2D images reconstructed along planes (or axes) other than the original acquisition plane are often better suited for visualizing a given abnormality.

As an alternative visualization means, the 3D viewing mode also presents another set of inherent limitations. For example, 3D sequences of images of an anatomical structure based on a pre-defined path have many limitations because the path is not always correct or feasible to compute due to occlusions or collapsed areas. In addition, the 3D view is often too narrow and provides little contextual information. Further, anatomical features of interest are often occluded by surrounding tissues or occluding material. For instance, in a virtual colonoscopy, polyps are often partially occluded by haustral folds, fluid and/or fecal material.

To address field-of-view limitations, the viewing angle can be expanded to present a broader panoramic view. Alternatively, the visibility can be expanded with bidirectional angles. As for limitations due to partial occlusion, these can be addressed by virtually unfolding the anatomical structure (e.g., colon) into a tubular structure and cutting it open to present a filet view. The virtual flythrough can be performed over the open structure or a curvy reconstruction of the tubular structure. These mechanisms, however, introduce much distortion and can be extremely ill-suited in most cases where the colon is not extremely well-distended, clean or insufflated. In addition, these methods require intensive real-time interactive capabilities as well as 3D rendering resources, which can limit their feasibility and deployment into viewing environments that are inherently 2D.

For the reasons stated above, and for other reasons stated below which will become apparent to those skilled in the art upon reading and understanding the present specification, there is a need in the art for more efficient, effective, and enhanced systems and methods for reviewing medical image data.

SUMMARY

In accordance with an aspect of the present invention, a technology is provided for enhanced visualization of medical image data. In one implementation, a region of interest is identified in a first set of images along at least one viewing direction, Based on the first set of images, a second set of images is reconstructed to include at least one selectively enhanced rendering of the region of interest. The selectively enhanced rendering may include a three-dimensional rendering or any other type of enhanced rendering to facilitate detection of abnormalities.

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Furthermore, it should be noted that the same numbers are used throughout the drawings to reference like elements and features.

DETAILED DESCRIPTION

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of a radiosurgery or radiotherapy procedure, which may include times when the radiation source is either on or off. From time to time, for convenience of description, CT imaging data may be used herein as an exemplary imaging modality. It will be appreciated, however, that data from any type of imaging modality including but not limited to X-Ray radiographs, MRI, CT, PET (positron emission tomography), PET-CT, SPECT, SPECT-CT, MR-PET, 3D ultrasound images or the like may also be used in various embodiments of the invention.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulate and transform data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

As used herein, the term "image" refers to multi-dimensional data composed of discrete image elements (e.g., pixels for 2D images and voxels for 3D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R or $R^7$, the methods of the inventions are not limited to such images, and can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

The following description sets forth one or more implementations of systems and methods that facilitate enhanced visualization of medical image data. One implementation of the present framework enhances visualization by processing a first set of images to reconstruct a second set of images in which certain regions of interest have been selectively enhanced by rendering. One or more external areas outside the regions of interest may remain substantially similar to corresponding areas in the first set of images. Alternatively, or in combination thereof, the external areas may be pre-processed to enhance visualization of any underlying structures by, for example, rendering clinically irrelevant structures as at least partially transparent. One of the advantages of the present framework is that it integrates the results of advanced rendering techniques into an established standard format (e.g., 2D image format) that can be read ubiquitously without requiring additional real-time rendering tools, hardware or other computational resources. Another major advantage is that it improves the workflow of the user (e.g., radiologist, physician, clinician, etc.) by enabling the detection of abnormal structures early in the image scrolling process, as will be described in more detail in the subsequent description.

It is understood that while a particular application directed to virtual colonoscopy may be shown, the technology is not limited to the specific embodiment illustrated. The present technology has application to, for example, visualizing features in other types of luminal, hollow or tubular anatomical structures (e.g., airway, urinary gall bladder, heart, blood vessel, trachea, intestine, etc.) or non-tubular objects, such as other organs or anatomical structures (e.g., liver, kidney, pancreas, brain, skeleton, breast, etc.). For instance, the present framework can be applied to images acquired for procedures such as colonography, enterography, airway imaging, vascular echography (e.g., for plaque characterization or pulmonary embolism diagnosis), neurography, lung imaging (e.g., lung parenchyma), breast imaging (e.g., mammography), pancreatic imaging, hepatic-imaging, urology or kidney imaging, neuroimaging (e.g., brain scan), skeletal imaging, and so forth.

Figure 1:
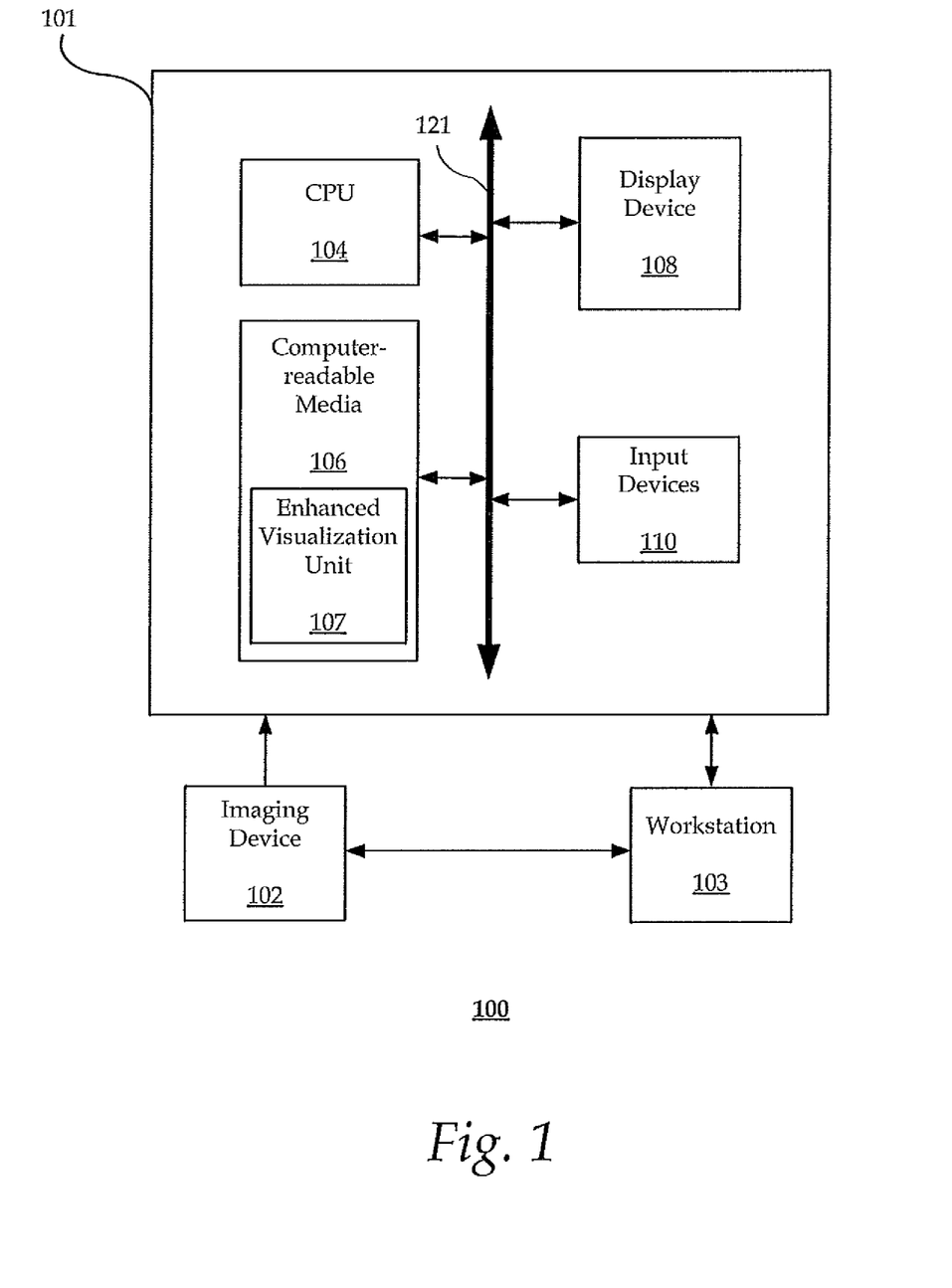
FIG. 1 shows an exemplary system.

FIG. 1 is a block diagram illustrating an exemplary system 100. The system 100 includes a computer system 101 for implementing the framework as described herein. The computer system 101 may be further connected to an imaging device 102 and a workstation 103, over a wired or wireless network. In one implementation, the imaging device 102 is a radiology scanner, such as a magnetic resonance imaging (MRI), computed tomography (CT), X-ray, ultrasound, positron emission tomography (PET), or a single photon emission computed tomography (SPECT) scanner, for acquiring image data.

Computer system 101 may be a desktop personal computer, a portable laptop computer, another portable device, a mini-computer, a mainframe computer, a server, a communications device, a storage system, a dedicated digital appliance, or another device having a storage sub-system configured to store a collection of digital data items. In one implementation, computer system 101 comprises a processor or central processing unit (CPU) 104 coupled to one or more non-transitory computer-readable media 106 (e.g., computer storage or memory), display device 108 (e.g., monitor) and various input devices 110 (e.g., mouse or keyboard) via an input-output interface 121. Computer system 101 may further include support circuits such as a cache, power supply, clock circuits and a communications bus.

It is to be understood that the present technology may be implemented in various forms of hardware, software, firmware, special purpose processors, or a combination thereof. In one implementation, the techniques described herein may be implemented as computer-readable program code tangibly embodied in the non-transitory computer-readable media 106. In particular, the techniques described herein may be implemented by enhanced visualization unit 107. The non-transitory computer-readable media 106 may include random access memory (RAM), read only memory (ROM), magnetic floppy disk, flash memory, and other types of memories, or a combination thereof. The computer-readable program code is executed by CPU 104 to process images (e.g., MR or CT images) from the imaging device 102 (e.g., MR or CT scanner). As such, the computer system 101 is a general-purpose computer system that becomes a specific purpose computer system when executing the computer readable program code. The computer readable program code is not intended to be limited to any particular programming language and implementation thereof. It will be appreciated that a variety of programming languages and coding thereof may be used to implement the teachings of the disclosure contained herein.

In one implementation, the computer system 101 also includes an operating system and microinstruction code. The various techniques described herein may be implemented either as part of the microinstruction code or as part of an application program or software product, or a combination thereof, which is executed via the operating system. Various other peripheral devices, such as additional data storage devices and printing devices, may be connected to the computer system 101.

The workstation 103 may include a computer and appropriate peripherals, such as a keyboard and display, and can be operated in conjunction with the entire system 100. For example, the workstation 103 may communicate with the imaging device 102 so that the image data collected by the imaging device 102 can be rendered and viewed on the display. The workstation 103 may include a user interface that allows the radiologist or any other skilled user (e.g., physician, technician, operator, scientist, etc.) to manipulate the image data. Further, the workstation 103 may communicate directly with the computer system 101 to display processed image data and/or output results for user interpretation. For example, the user may use an input device (e.g., mouse, keyboard, touch screen, etc.) at the workstation 103 (or system 101) to scroll up and down a stack of 2D images following a mental picture of an anatomical structure (e.g., colon) to manually detect any abnormality indicative of a medical condition of interest (e.g., cancer).

Figure 2:
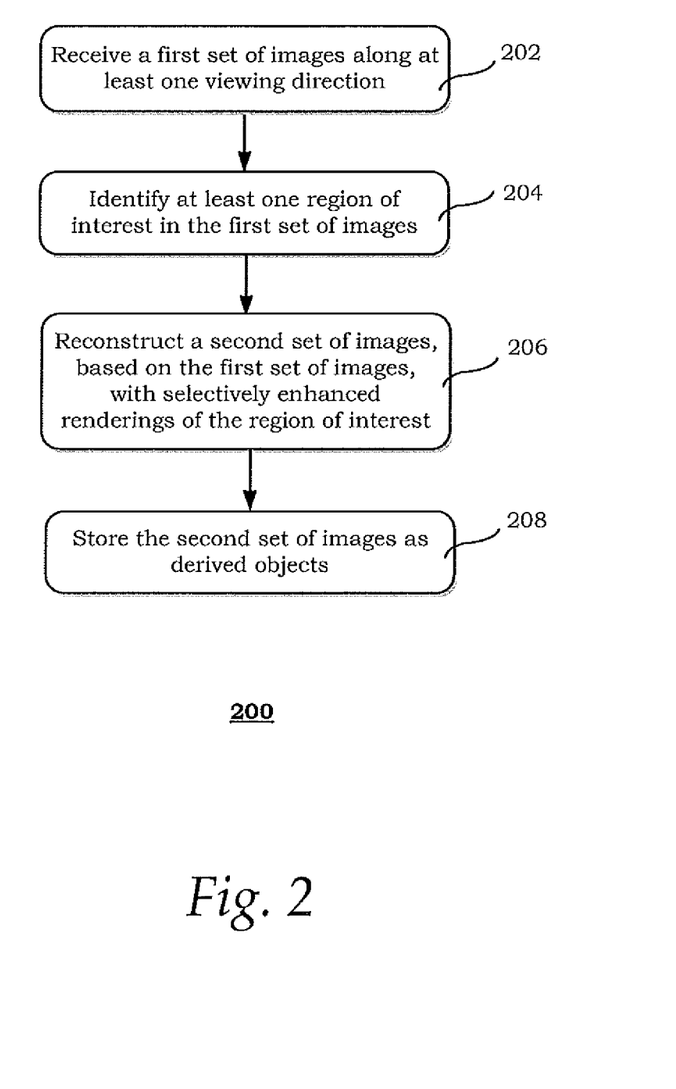
FIG. 2 shows an exemplary method of visualization.

FIG. 2 shows an exemplary method 200 of enhanced visualization in accordance with one implementation of the present framework. The exemplary method 200 may be implemented by the enhanced visualization unit 107 in the computer system 101, previously described with reference to FIG. 1.

At 202, a first set of images along at least one viewing direction is received by the enhanced visualization unit 107. The images may be received from, for example, a storage device, database system or an archiving system, such as a picture archiving and communication (PAC) system. The images may be reconstructed from stored data acquired by, for example, the imaging device 102 using techniques such as magnetic resonance (MR) imaging, computed tomography (CT), helical CT, x-ray, positron emission tomography, fluoroscopic, ultrasound, single photon emission computed tomography (SPECT), etc. Such data can be acquired via a procedure for colonography, enterography, airway imaging, vascular echography, neurography, lung imaging, breast imaging, pancreatic imaging, hepatic-imaging, urology or kidney imaging, neuro-imaging, skeletal imaging, or any other type of application.

In one implementation, the images are synthesized from stored data along a viewing direction, which is the direction in which a theoretical lens points. The theoretical lens may correspond to the lens of a virtual endoscope or any other theoretical instrument within the subject's body. Stated another way, the images presented at any time may correspond to the images which would have been seen by the theoretical instrument having a lens at a given location relative to the instrument. In addition, the images may be generated based on one or more viewing characteristics specified by the user. For example, the user may specify the viewing direction, the field of view, location of the theoretical lens within the subject's body, etc. Alternatively or additionally, the viewing characteristics can be automatically determined or defined based on specific protocols.

The images may present orthogonal views (e.g., axial, coronal and sagittal), which are normally used in 2D viewing modes for clinical review. Alternatively, the images may represent trajectory views, taken on a plane perpendicular to the axis of the instrument, looking from outside the subject, or perpendicular views, taken on a cutting plane that is perpendicular to the axis of the theoretical instrument. It is understood that any other types of views may also be presented. In addition, the images may be binary (e.g., black and white) or grayscale, with intensity values indicative of certain material properties of the subject, such as radiodensity values measured in Hounsfield Units. Pre-processing may be performed on the images, either automatically by the computer system 101 or manually by a skilled user (e.g., radiologist). For example, the images may be pre-filtered to remove noise artifacts or to enhance the quality of the images for ease of evaluation. Other types of pre-processing may also be performed.

At 204, at least one region of interest (ROI) is identified in the first set of images for enhancement. An ROI is a sub-area or sub-volume of the image that has been identified for further study and examination. In one implementation, the ROI represents at least a portion of a lumen, such as the internal wall of a luminal (or tubular) structure. Examples of luminal structures include, for instance, a colon, artery, blood vessel, heart, airway, lung, intestine, gall bladder, etc. The ROI may also represent a portion of other types of non-luminal organs or anatomical structure, such as the brain, skeletal structure, breast, pancreas, liver, and so forth. The ROI may represent either a normal (i.e. healthy) or abnormal structure. To automatically detect the ROI, the computer system 101 may use an image processing technique, such as one that detects points where the change in intensity exceeds a certain threshold. Alternatively, the ROI may be manually identified by a skilled user via, for example, a user-interface at the workstation 103.

At 206, a second set of images are reconstructed or derived based on the first set of images. Each image in the second set of images may be reconstructed from one or more corresponding images in the first set of images to include a selectively enhanced rendering of the previously identified region-of-interest (ROI). For example, the enhanced rendering may be three-dimensional (3D) while the area outside the ROI is two-dimensional (2D). In other words, the reconstructed image can be referred to as "two-and-a-half-dimensional" (or 2½ D). Multiple different types of enhanced renderings may be generated for multiple regions-of-interest (ROIs). In addition, one or more areas outside the ROIs may be pre-processed to achieve de-emphasis relative to the ROIs, as will be described later.

To generate the enhanced rendering, various rendering techniques, such as shading (e.g., flat, Gouraud, Phong shading, etc.), texture mapping, bump mapping, ray tracing, radiosity, subsurface scattering, etc., may be employed. For example, a 3D enhanced rendering may roughly correspond to a photorealistic image of the structure represented by the ROT. Other types of rendering techniques, such as maximum or minimum intensity projections over regions of varying depths, may also be applied. The rendering may be performed relative to, for example, the normal viewing orientation of the set of images, or other viewing directions. The viewing direction may be determined manually or automatically so as to optimize the field of view and/or coverage.

Figure 3A:
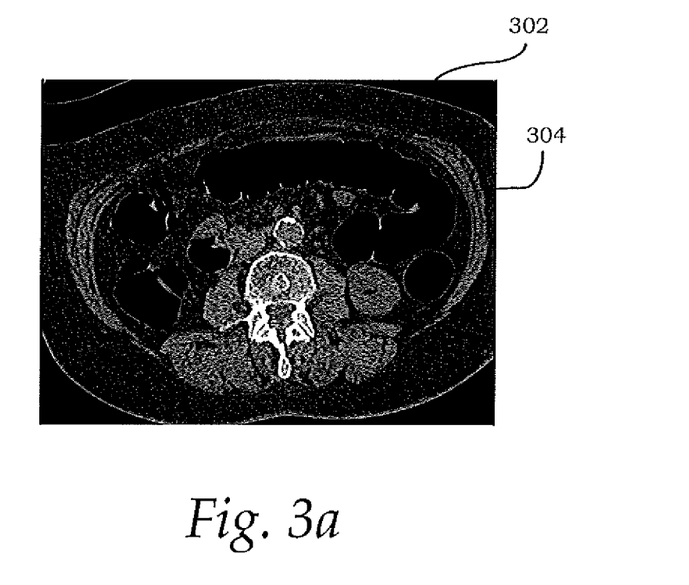
FIG. 3a shows a traditional colonography image and FIG. 3b shows an exemplary enhanced colonography image in accordance with one implementation.
Figure 3B:
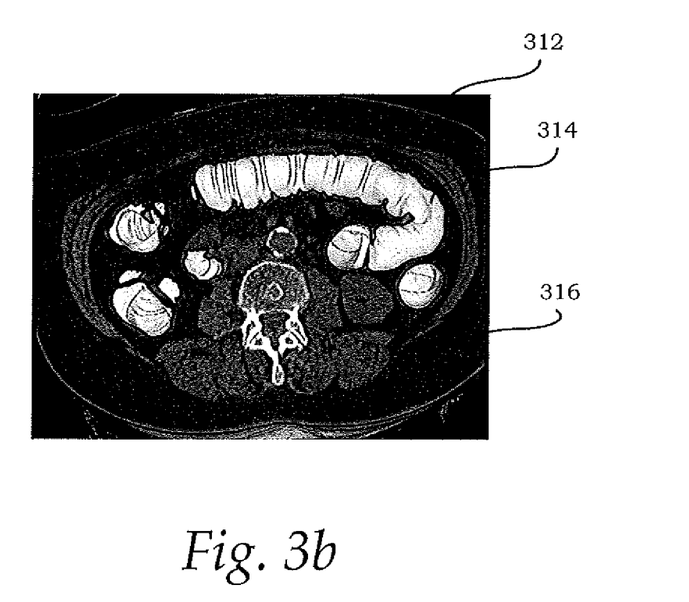

FIGS. 3*a-b* illustrate the application of enhanced rendering to CT colonography. FIG. 3*a* shows a 2D cross-sectional axial image 302 acquired during an abdominal scan. As typically seen via a 2D viewer software, the lumen 304 of the colon appears black. FIG. 3*b* shows an exemplary two-and-a-half-dimensional (2½ D) image 312 derived from the 2D image 302 in accordance with the present framework. Areas of the lumen (or colon wall) 314 are presented in three-dimensional enhanced renderings, while other areas 316 outside of the lumen remain as two-dimensional renderings. While scrolling through the stack of images and tracking the colon to detect any polyps or abnormal structures, the user will be able to preview areas within the lumen, including the underlying structure of the wall and folds protruding into the lumen.

The enhanced rendering in the reconstructed image may further be generated by combining multiple images of the first set of images. For example, 10 to 50 slices from the first set may be combined to reconstruct an image in the second set. In one implementation, the enhanced rendering represents a structure that is visible only in a subset of the multiple images used to reconstruct the image. Such enhanced rendering will allow the user to view a few slices below the top rendered slice so as to visualize a structure that is visible only at a given depth. This type of visualization advantageously allows the user to inspect the boundary or outer profile of the anatomical structure for any abnormal deformation. In the context of skeletal imaging, for example, the user may be able to see the cross-section of a 3D enhanced rendering of the profile of the rib, as well as beyond and outside the rib area. It can also be applied to other clinical applications, such as visualizing lung parenchyma, aneurysms in arteries, and so forth.

Alternatively, or in combination thereof, the enhanced rendering may be generated by applying a transfer function to accentuate (or emphasize) certain clinically relevant areas and/or de-emphasize clinically irrelevant areas. For example, the transfer function may cause both dark areas and areas with contrast to be displayed as transparent. Alternatively, or additionally, the enhanced rendering process may treat the dark areas as transparent and filling defects (e.g., protrusions into the lumen) in accordance with intensity characteristics. For instance, the filling defects may be color-coded according to density. In the context of virtual colonoscopy, for example, the colon wall may be rendered as semi-transparent, while the underlying tissue and tagged fecal material may be color-coded in accordance with a color scheme for direct differentiation. It should be appreciated that other types of transfer functions may also be applied.

In one implementation, solid organs or lumen are rendered as semi-transparent or transparent for purposes of visualizing any underlying structures. For example, the enhanced rendering may treat normal organ parenchyma as partially transparent so as to reveal particular structures, vessels or lesions within it. Therefore, unlike a conventional virtual flythrough, the desired structure (or tissue) is "thinned out" to achieve better visualization of underlying structures. In the context of skeletal imaging, for instance, the enhanced rendering may display the skeletal structure (or bone) as a solid (or non-transparent) structure while the non-skeletal portions are presented as semi-transparent. This is to achieve better visualization and emphasis of bone lesions, such as lytic, sclerotic and blastic lesions. The skeletal structure may also be de-emphasized relative to surrounding tissues to better reveal other structures or lesions which would be otherwise occluded or obfuscated.

In another example, images of the brain may be reconstructed so as to render certain portions of the brain as transparent to reveal various underlying structures, such as the ventricles, the hypothalamus, or gray matter in contrast to white matter. Such visualization may be important for monitoring changes in, for example, gray or white matter integrity in patients with Alzheimer's disease or other neurological diseases. Other applications include visualization of breast MRI data by generating 3D sequences of composite uptakes. A further application involves mammograms or breast tomographic sequences, where the normal parenchyma is de-emphasized (or made semi-transparent) to reveal structures or lesions of interest (e.g. calcification). This capability may be of particular importance in cases of dense breast tissue.

In one implementation, one or more areas outside the ROI are pre-processed to generate a type of rendering that is different from the selective enhanced rendering of the ROI so as to complement the visual enhancement of the ROI. For example, the areas outside the ROI may be de-emphasized by rendering at least one clinically irrelevant structure as partially transparent. As previously discussed with respect to the enhanced rendering, a transfer function may also be applied to render voxels outside the ROT as at least partially transparent. For example, muscle or bone structures outside the ROI may be presented as solid surfaces, while vascular structures are presented as semi-transparent or transparent to reveal any underlying structures. Alternatively or additionally, areas outside the ROI may be pre-processed to highlight (or accentuate) any structure that has a physical property that is different from the ROI. For instance, proximate areas outside the ROI may be visually highlighted if they represent structures that have thicknesses different from the ROT, To achieve the highlighting, a filter or transfer function based on intensity values (e.g., Hounsfield units) may be applied to generate a different color, shading, texture, or other distinguishable visual effect.

Alternatively, or in combination thereof, one or more areas outside the ROI may remain substantially unchanged or similar to corresponding areas in the first set of images. For example, the areas outside the ROI may remain as 2D while the enhanced rendering of the ROI is 3D. In addition, further processing may be performed to, for example, center the second set of images with respect to the ROI. For instance, in the context of colonoscopy, the enhanced images may be centered with respect to the colon or lumen.

The second set of images may also include pre-rendered composite images, each having 2 or more sub-images with enhanced renderings of the region of interest in accordance with the present framework. The sub-images may be reconstructed by using different viewing characteristics, such as viewing direction, virtual camera position, angle of view, virtual light source position, etc. For example, the viewing directions of the sub-images may be opposite to each other (e.g., head-to-feet & feet-to-head, front-to-back & back-to-front) as seen from the same cross-section or slice. The viewing directions may also be orthogonal or at any other angle in relation to each other. By providing such pre-rendered composite images, different views of the same ROI can be automatically synchronized, stored and retrieved without requiring any additional real-time processing or resources.

Figure 4:
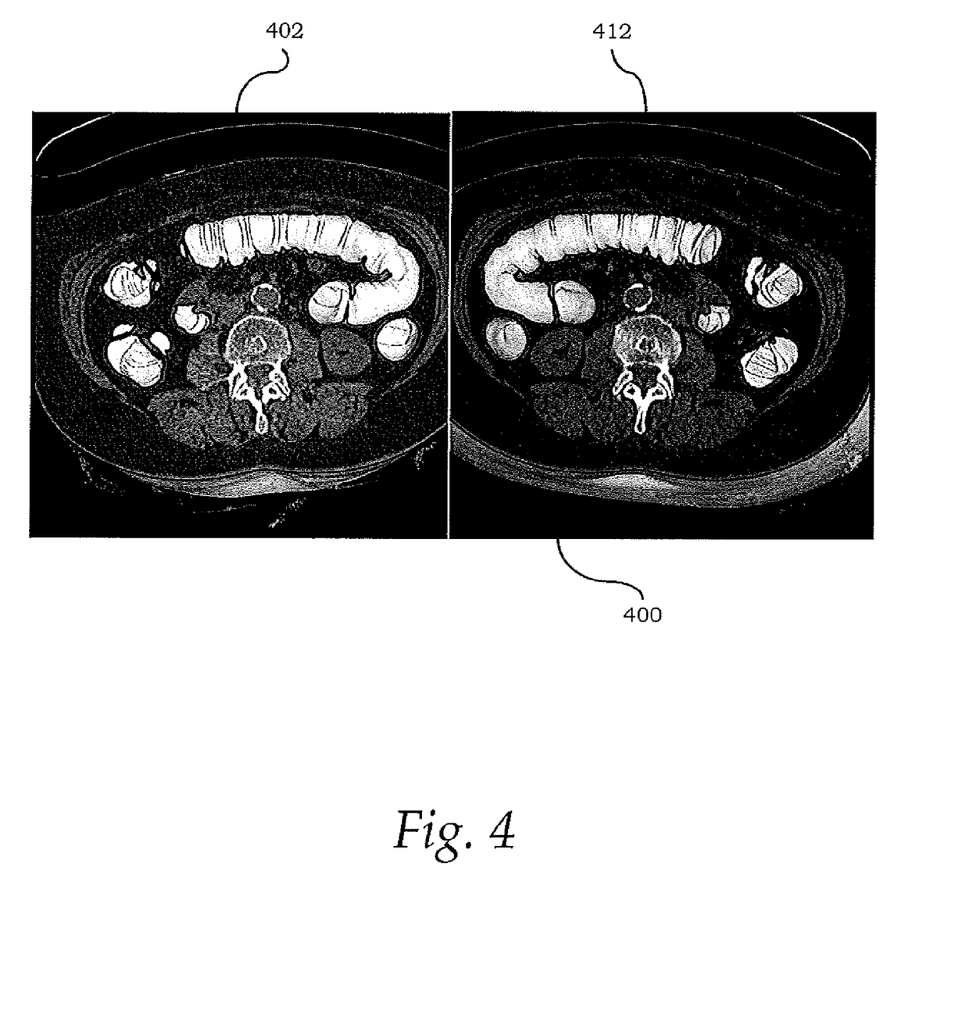
FIG. 4 shows an exemplary composite enhanced image in accordance with one implementation.

FIG. 4 illustrates an exemplary composite image 400 that includes a 2½ D sub-image 402 generated in the head-to-feet direction and another 2½ D sub-image 412 generated in the feet-to-head direction. While the user scrolls through the stack of enhanced images, the user will be able to see both views as part of the same image 400. For exemplary purposes, the image 400 is displayed as a composite in left-right mirror layout. It is understood that other layouts may also be generated. For example, a top-bottom layout that provides the effect of flipping the images as the user scrolls through the stack of enhanced images can also be employed. As yet another example, non-mirror side-to-side layouts can also be used.

At 208, the second set of images is stored as derived objects in a storage device (e.g., non-transitory computer readable media 106). The storage device may include, or be communicatively coupled to, an archiving or database system, such as the PAC system of a hospital, a healthcare facility or other institution. The derived objects are data structures that can be stored in any suitable file format. For example, the file format may be a standard format compliant with the Digital Imaging and Communications in Medicine (DICOM) standard. It should be appreciated that other types of file formats may also be used.

When the reconstructed images are needed for viewing, the derived objects are retrieved from the storage device and viewed on, for example, display device 108. Since the enhanced renderings have already been pre-generated at, for example, step 206, the derived objects can be displayed using any standard processor, graphics card or other available hardware or software, without requiring additional real-time rendering resources. The reconstructed images may be viewed using Web-based visualization tools, PAC system, workflow software or any other platforms. For example, the images may be viewed on a mobile device with a Web-based or multimedia visualization platform (e.g., Adobe Flash Player). The reconstructed images may further be transformed or compressed for more efficient transmission to the desired platform.

In one implementation, the reconstructed images are used to improve the workflow of a physician, radiologist, clinician, any other healthcare professional or user. Generally, workflows are dependent on the protocols and type of structures under review. However, visual inspections of most anatomical structures have the following commonality—axial review to track the anatomical structure from one end to the other end to identify or characterize any suspicious physical abnormalities. A physical abnormality may be characterized as, for example, a protrusion (e.g., polyp, arterial plaque, thickening of the lining of a wall, etc.) or a depression (e.g., diverticuli, aneurysms, etc.) in the wall of the structure of interest. Since the axial view is not naturally the optimal or sufficient way of cutting through the structure, the workflow may require the user to scroll up and down a stack of images (or slices) as a means to mentally visualize the complete volume of the anatomical structure and detect any physical anomalies.

For example, in the context of CT colonoscopy, the detection of a polyp is effectively based on the observation of a sudden appearance of the outline of a protruding structure into the lumen. Depending on the presence of contrast agent, the polyp may appear to be black or white. When the colon is well distended and prepped, this review process can be performed efficiently. However, the success of such review is very dependent on the ability of the radiologist to notice such protrusions, which are often subtle. Given the extent of the colon, the number of folds and the sudden visibility of the polyps, it requires the physician to be most attentive to subtle and progressive deformation of the contour of the colon wall. In fact, the majority of initially observed protrusions are actually normal anatomical structures, known as folds, which may initially present themselves as pseudo polyps or false positives. Polyps, on the other hand, are mostly characterized by the appearance and sudden disappearance, rather than folds, which slowly fade in and out during the scrolling process. Similarly, when considering lung parenchyma, vessels appear at cross-sections in a manner very similar to nodular structures. However, similar to folds, they linger through multiple slices during the scrolling process, rather than appear and disappear as nodules. Therefore, an enhanced rendered view that shows the lung parenchyma across, for example, 10 or 20 slices, enables a good review that focuses on nodules and de-emphasizes other irrelevant structures. It is understood that the same approach can be applied when detecting other types of abnormal structures, such as pulmonary embolism.

Enhanced images that are reconstructed in accordance with the present framework may accentuate the presence of any physical abnormality and allow the user to easily track the anatomical structure during the scrolling process. Moreover, enhancement integrated within the images provides a means for maintaining proper anatomical context and information. For example, in the context of reviewing lumen areas, any physical abnormality within the lumen will appear well in advance in the scrolling process. In addition, the abnormality will more likely be detected because it will persist (or remain visible) for a longer period of time during the scrolling review process. By allowing a reviewer to focus on areas of interest, and move expeditiously through unremarkable or clinically irrelevant areas, review time can be greatly reduced. In addition, the visualization of the 3D anatomical structures can be provided through the use of ubiquitous and established mechanisms to review 2D images, without requiring additional real-time rendering resources.

Figure 5:
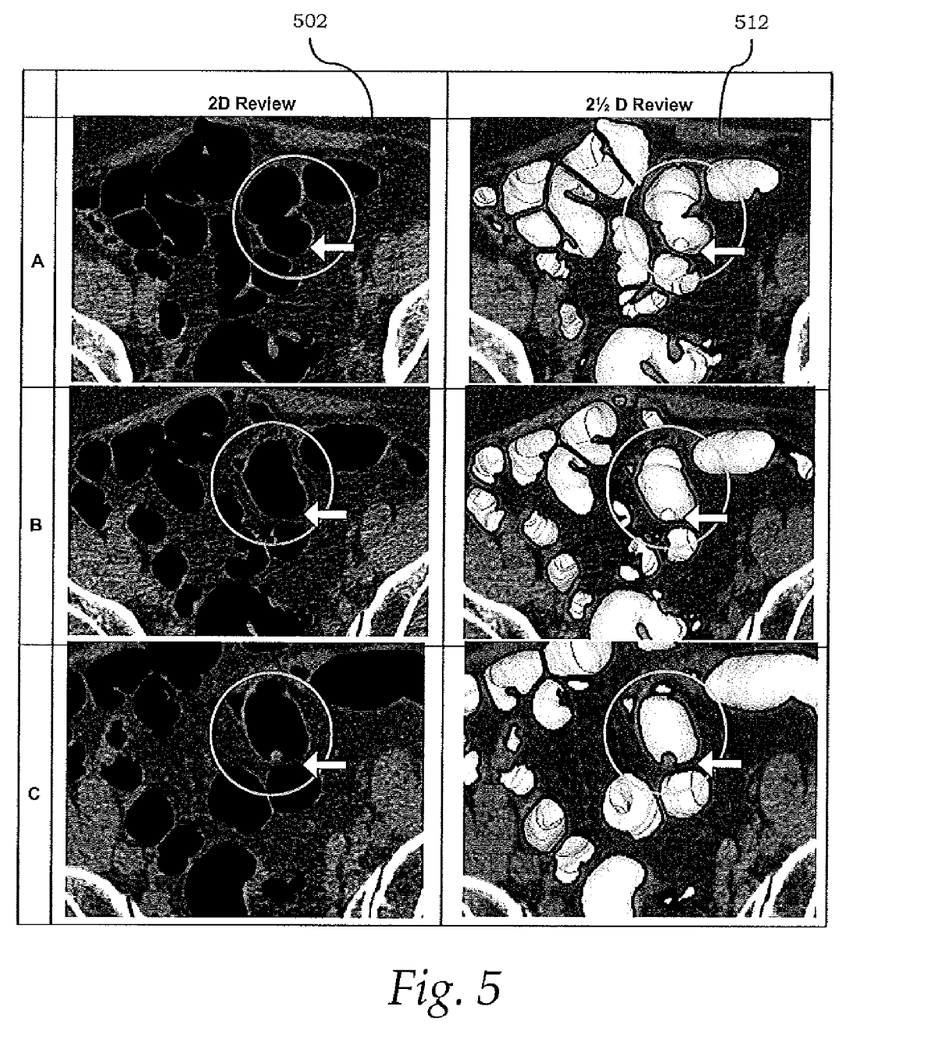
FIG. 5 shows a comparison of a traditional 2D image review workflow with an exemplary enhanced image review workflow.

To illustrate how 2½ D images resulting from the present framework may assist the user in efficiently reviewing a dataset, FIG. 5 compares a sequence of images 502 (left column) for a traditional 2D CT colonography workflow with a sequence of enhanced images 512 (right column) for a 2½ D CT colonography workflow in accordance with the present framework. Both workflows involve the user scrolling through the sequence of images (502 or 512), while following the anatomical structure of the colon from the rectum to the caecum with the goal of detecting colonic polyps. The circle indicates the area of focus while the arrow indicates where the polyp will likely appear.

By using 2D review (left column), it is only with row C, more than 15 slices from row A, that the polyp becomes visible. The enhanced 2½ D review (right column), however, allows the user to see the polyp ahead of time (at row A) and be better prepared to detect it. Moreover, it can be observed that the visibility of the polyp is persisting over many slices (rows A, B, C), thereby advantageously allowing more time for the user to detect it. In addition, the polyp is more likely to be detected since both the 3D morphological characteristics of structures in the lumen as well as the cross-sectional 2D internal characteristics of the structures are accentuated.

Although the one or more above-described implementations have been described in language specific to structural features and/or methodological steps, it is to be understood that other implementations may be practiced without the specific features or steps described. Rather, the specific features and steps are disclosed as preferred forms of one or more implementations.

Further, although method or process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

Although a process may be described as including a plurality of steps, that does not indicate that all or even any of the steps are essential or required. Various other embodiments within the scope of the described invention(s) include other processes that omit some or all of the described steps. Unless otherwise specified explicitly, no step is essential or required.

The invention claimed is:

1. A system for visualizing medical image data, comprising:
    a memory device for storing non-transitory computer readable program code; and
    a processor in communication with the memory device, the processor being operative with the computer readable program code to:
        (i) receive a first set of images of a subject along at least one viewing direction, wherein the first set of images is acquired by magnetic resonance (MR) imaging, computed tomography (CT), helical CT, x-ray, positron emission tomography, fluoroscopic, ultrasound or single photon emission computed tomography (SPECT);
        (ii) identify at least one region of interest in the first set of images;
        (iii) reconstruct a second set of images of the subject based only on the first set of images, wherein a single composite image in the second set of images comprises at least two adjacent sub-images reconstructed by using different viewing characteristics, wherein each of the two adjacent sub-image includes at least one selectively enhanced three-dimensional rendering of the region of interest and two-dimensional rendering of one or more areas outside the region of interest; and
        (iv) store the reconstructed second set of images in two-dimensional image format in an archiving system.

2. The system of claim 1 wherein the at least one region of interest represents at least one portion of a lumen.

3. The system of claim 1 wherein the at least one region of interest represents at least one portion of a skeletal structure.

4. The system of claim 1 wherein the at least one region of interest represents at least one portion of an organ.

5. The system of claim 1 wherein the selectively enhanced rendering presents one or more filling defects as color-coded according to intensity characteristics.

6. The system of claim 1 wherein the selectively enhanced rendering presents at least a portion of the region of interest as at least partially transparent to reveal any underlying structure.

7. The system of claim 6 wherein the region of interest comprises normal parenchyma or a skeletal structure.

8. The system of claim 1 wherein the processor is further operative with the computer readable program code to reconstruct at least one image of the second set of images with the selectively enhanced rendering by combining multiple images of the first set of images.

9. The system of claim 8 wherein the selectively enhanced rendering represents at least one structure that is visible in a subset of the multiple images.

10. The system of claim 1 wherein the one or more areas outside the region of interest remain substantially similar to corresponding one or more areas in the first set of images.

11. The system of claim 1 wherein the processor is further operative with the computer readable program code to pre-process at least one area outside the region of interest by rendering at least one clinically irrelevant structure as at least partially transparent.

12. The system of claim 1 wherein the processor is further operative with the computer readable program code to pre-process at least one area outside the region of interest to highlight a first structure associated with a physical property that is different from a second structure represented by the region of interest.

13. The system of claim 1 wherein the at least one viewing direction comprises an axial, coronal or sagittal viewing direction.

14. The system of claim 1 wherein the first set of images is acquired via a procedure selected from colonography, enterography, airway imaging, vascular echography, neurography, lung imaging, breast imaging, pancreatic imaging, hepatic-imaging, urology or kidney imaging, neuro-imaging or skeletal imaging.

15. The system of claim 1 wherein the first set of images is received from an archiving system.

16. The system of claim 1 wherein the processor is further operative with the computer readable program code to pre-process the first set of images.

17. The system of claim 1 wherein the processor is further operative with the computer readable program code to generate the enhanced rendering by performing a shading technique, texture mapping, bump mapping, ray tracing, radiosity, subsurface scattering technique, maximum or minimum intensity projections.

18. The system of claim 1 wherein the region of interest in the first set of images represents at least one abnormal anatomical structure.

19. The system of claim 1 wherein the different viewing characteristics comprise feet-to-head and head-to-feet viewing directions.

20. The system of claim 1 wherein the different viewing characteristics comprise different viewing directions.

21. The system of claim 1 wherein the different viewing directions comprise front-to-back and back-to-front viewing directions.

22. The system of claim 1 wherein the processor is further operative with the computer readable program code to center the second set of images with respect to the region of interest.

23. A non-transitory computer readable medium embodying a program of instructions executable by machine to perform steps for visualization of image data, the steps comprising:
  (i) receiving a first set of images of a subject along at least one viewing direction, wherein the first set of images is acquired by magnetic resonance (MR) imaging, computed tomography (CT), helical CT, x-ray, positron emission tomography, fluoroscopic, ultrasound or single photon emission computed tomography (SPECT);
  (ii) identifying at least one region of interest in the first set of images;
  (iii) reconstructing a second set of images of the subject based only on the first set of images, wherein a single composite image in the second set of images comprises at least two adjacent sub-images reconstructed by using different viewing characteristics, wherein each of the two adjacent sub-image includes at least one selectively enhanced three-dimensional rendering of the region of interest and one or more areas outside the region of interest that are rendered in two dimensions; and
  (iv) storing the reconstructed second set of images in two-dimensional image format in an archiving system.

24. A method of visualizing medical image data, comprising:
  (i) receiving a first set of images of a subject along at least one viewing direction, wherein the first set of images is acquired by magnetic resonance (MR) imaging, computed tomography (CT), helical CT, x-ray, positron emission tomography, fluoroscopic, ultrasound or single photon emission computed tomography (SPECT);
  (ii) identifying at least one region of interest in the first set of images;
  (iii) reconstructing a second set of images of the subject based only on the first set of images, wherein a single composite image in the second set of images comprises at least two adjacent sub-images reconstructed by using different viewing characteristics, wherein each of the two adjacent sub-image includes at least one selectively enhanced three-dimensional rendering of the region of interest and one or more areas outside the region of interest that are rendered in two dimensions; and
  (iv) storing the reconstructed second set of images in two-dimensional image format in an archiving system.

* * * * *